United States Patent
Cloyd et al.

(10) Patent No.: US 6,448,014 B2
(45) Date of Patent: Sep. 10, 2002

(54) PCR-HYBRIDIZATION ASSAYS SPECIFIC FOR INTEGRATED RETROVIRUSES

(75) Inventors: Miles W. Cloyd, Galveston, TX (US); Chi-Cheng Yeh, Richardson, TX (US); Jianmin Chen, Galveston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/837,149

(22) Filed: Apr. 18, 2001

Related U.S. Application Data (60) Provisional application No. 60/198,884, filed on Apr. 19, 2000.

(51) Int. Cl.[7] ............ C12Q 1/68; C12P 19/34; C07H 21/04
(52) U.S. Cl. ............ 435/6; 495/91.2; 536/24.33
(58) Field of Search ............ 435/6, 91.2; 536/22.1, 536/24.33

(56) References Cited

U.S. PATENT DOCUMENTS 5,538,871 A * 7/1996 Nuovo et al. ............ 435/91.2

OTHER PUBLICATIONS

Fritsch et al. Production of HIV–1 by huamn B cells infected in vitro: Characterization of an EBV genome–negative B cell line chronically synthesizing a low level of HIV–1 after infection. Virology, vol. 244: 542–551, 1998.*

Carteau et al. Chromosome structure and human Immunodeficiency virus type 1 cDNA integration: centromeric alphoid repeats are a disfavored target. J. Virol., vol. 72(5): 4005–4014, 1998.*

Carteau S et al. Chromosome structure and human Immunodeficiency virus type 1 cDNa integration: centromeric alphoid repeats are a disfavored target. J Viorology, 72(5): 4005–4014, 1998.*

Embretson J et al. Analysis of human immunodeficiency virus–infected tissues by amplification and in situ hybridization reveals latent and permissive infections at single–cell resolution. Proc.Natl.Acad.Sci.USA., 90: 357–361, 1993.*

Statagene Catalog.Gene characterization kits. p. 39, 1998.*

* cited by examiner

*Primary Examiner*—Jeffrey Fredman
*Assistant Examiner*—Prabha Chunduru
(74) *Attorney, Agent, or Firm*—Benjamin Aaron Adler (57) ABSTRACT

The present invention provides a method of determining latent HIV infection by detecting low-abundant HIV nucleic acid sequences in samples of cellular DNA or in paraffin-fixed tissue sections or frozen sections. This technique calls for one primer for an Alu sequence in the human chromosomal DNA and the other primer near the end of the viral LTR. PCR-amplified DNA is then hybridized with a probe which only recognizes the amplified LTR sequence. This probe could be labeled in different ways, and quantitative assays for latent HIV or other retroviruses infection could be developed.

1 Claim, 8 Drawing Sheets

Fig. 2C uninfected PBLs

HIV infected PBLs latent PBLs

Fig. 3A

Fig. 3B uninfected, resting PBLs

HIV infected, resting PBLs uninfected, PHA-stimulated PBLs

HIV infected, PHA-stimulated PBLs

PCR-HYBRIDIZATION ASSAYS SPECIFIC FOR INTEGRATED RETROVIRUSES

CROSS-REFERENCE TO RELATED APPLICATIONS

This non-provisional application claims benefit of priority of U.S. provisional No. 60/198,884, filed Apr. 19, 2000, now abandoned.

BACKGROUND OF THE INVENTION

1. Field of the Invention

The present invention relates generally to the fields of virology and diagnostics. More specifically, the present invention relates to the development of PCR-hybridization assays specific for integrated retroviruses and their use in the determination of latent infection in patients.

2. Description of the Related Art

It has been known for many years that latent HIV infection can occur in infected cell lines in vitro and nearly all of the early studies of the molecular mechanisms underlying HIV latency examined what is occurring in latently infected clonally derived T-cell lines (2–4, 10, 13, 15). It was also demonstrated many years ago that there is a considerably greater frequency (~100-fold more) of lymphocytes in HIV patients which contain HIV DNA than cells which are productively infected (i. e., possess HIV DNA as well as making HIV RNA, viral proteins, and progeny virions) (6, 7). Studies examining HIV infection of resting or activated CD4 lymphocytes in vitro clearly showed that only activated cells are primarily permissive for virus replication and allow progeny virus production, and infection of resting cells usually leads an abortive infection, in which the virus binds, enters, and completely or partially reverse transcribes proviral DNA. This viral DNA, however, does not integrate until the cell is activated into division within a few days (9, 17). Most of the relatively higher frequency of HIV $DNA^+/RNA^-$ lymphocytes in HIV patients (~0.8%) (5), therefore, are very likely recently infected (abortively) resting lymphocytes. This should be expected since 99% of all lymphocytes are resting (16). However, some of these HIV $DNA^+/RNA^-$ cells found in infected subjects may also be latently infected cells, and these cells would have integrated proviral DNA but are not making progeny virus. The frequency of latently infected cells in $HIV^+$ individuals is not clear.

Studies in vitro examining acute and chronic infection of both human T-cell lines and PHA-stimulated CD4 PBLs has shown that gradual shutdown of the virus into latency is routine for the majority of acutely infected cells, and shutdown into latency should be considered a normal part of the virus life cycle (11). Thus, in an HIV patient, any productively infected cells, which are not eliminated by the immune system or by replication of cytopathic HIVs, should become latently infected cells. Thus, it is possible that reliable quantitative data on the frequencies of latently infected cells in patients may reveal that there exists a large pool of such cells.

One study attempted to directly quantitate the frequency of latently infected cells in HIV patients using an inefficient re-ligation technique of PCR-amplified HIV-cellular DNA and found that the frequency was low: at approximately the same frequency as productively-infected cells (~7 cells per $10^6$) (5). More recent studies have used limiting dilution culturing of lymphocytes from patients, which are activated by PHA to reactivate latent virus. The frequencies of these cells are much higher (8). Unfortunately, this procedure also allows any recently abortively infected resting cells to complete the virus replication cycle and become HIV-producing cells, and thus those studies do not discriminate completely between the abortively infected cells and latently infected cells.

Understanding the extent of latent infection has become of great importance now because HAART therapy can reduce plasma viral loads for long periods of time, yet when the drugs are removed, virus usually returns. It seems reasonable to conjecture that a great deal of this return is due to reactivation of HIV from latently infected cells.

The prior art is deficient in the lack of effective means of detecting latent HIV infection in patients. The present invention fulfills this long-standing need and desire in the art.

SUMMARY OF THE INVENTION

The present invention describes an in situ PCR assay that only detects integrated retroviruses, and this should allow accurate assessment of the frequency of productively and latently infected cells together in patients. Since the frequencies of productively infected cells at any given time in patients is known to be very low, any larger frequencies would have to be measuring latent infection. Through the use of PCR and hybridization, a new way to score for integrated retroviruses in cellular chromosomal DNA is possible. This method may be adapted in many forms of quantitative assays of latent HIV infection in infected subjects undergoing anti-retroviral drug therapy and should allow physicians to monitor the presence of latently infected cells so that they can determine whether treatment should be discontinued or not.

The invention utilizes PCR and employs one primer for an Alu sequence in the human chromosomal DNA and the other primer near the end of the viral LTR. PCR-amplified DNA is then hybridized with a probe which only recognizes the amplified LTR sequence. The probe could be labeled in different ways, and numerous forms of this test could be developed, many of which could be quantitative.

In one aspect of the present invention, there is provided a quantitative PCR assay to measure HIV latent infection.

In another aspect of the present invention, there is provided a kit for detecting integrated retroviruses in a human sample.

In another embodiment, the invention can be used to monitor latent infection by other retroviruses.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Assessment of whether cells possess integrated retrovirus in their chromosomal DNA is relatively straight-forward when all the cells examined have at least one viral copy. This can be accomplished by routine Southern blot hybridization techniques of either uncut or restriction enzyme digested chromosomal DNA. However, in the case of HIV infection, much less than 1% of cells contain integrated retroviruses, and PCR techniques have to be used.

Figure 1:
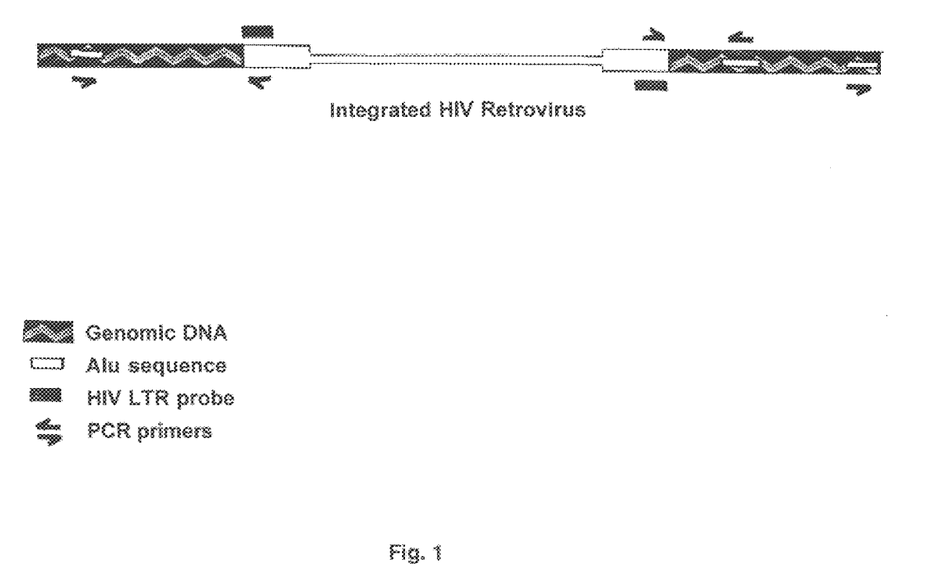
FIG. 1 shows primer design and probe hybridization. One primer lies in an alu sequence in the human chromosomal DNA and the other primer is located near the end of the viral LTR. PCR amplified DNA is then hybridized with a probe which only recognizes the amplified LTR sequence.

Currently, clinicians can only monitor newly produced virus by the quantitative RT-PCR assays or the presence of HIV DNA by PCR (99% of which represents abortive infection of newly infected cells and not cells making virus). There is no easy way to monitor the extent of latent infection. The present invention is a new way to score for integrated retroviruses in cellular chromosomal DNA, which could be exploited for quantitative assays of productive plus latent HIV infection in patients undergoing anti-retroviral drug therapy. This technique utilizes PCR for the detection of low-abundant HIV nucleic acid sequences only in cellular DNA and is described in in situ assays on paraffin-fixed tissue sections or frozen sections, although it could be used in any number of formats. The invention features one primer for an Alu sequence in the human chromosomal DNA and the other primer near the end of the viral LTR (see FIG. 1). PCR-amplified DNA is then hybridized with a probe which only recognizes the amplified LTR sequence. Numerous forms of this test could be developed, many of which could be quantitive.

The DNA hybridization probe can be labelled by any of the many different methods known to those skilled in this art. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA Blue and Lucifer Yellow. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. Those of ordinary skill in the art will know of suitable labels which may be employed in accordance with the present invention.

In one embodiment of the present invention, there is provided a quantitative method of detecting integrated retroviruses in a human sample by first amplifying DNA in the sample with PCR using one primer for an Alu sequence and the other primer for a retroviral sequence. Preferably, the primer for the Alu sequence has the sequence of 5'-TCCCAGCTACTGGGGAGGTGAGG-3' (SEQ ID NO: 1), and the primer for the retroviral sequence recognizing the 5' LTR sequence of HIV has the sequence of 5'-AAGCTCGATATCAGCAGTTCT-3' (SEQ ID NO: 2). Alternatively, a primer for the 3' LTR (such as 5'-CAGCTGCTTTTTGCCTGTACTG-3', SEQ ID NO: 3) could be used. The PCR-amplified DNA is then hybridized with a probe that specifically recognizes the amplified retroviral sequence. Preferably, the samples are paraffin-embedded sections or frozen sections of blood, lymph nodes or lymphocytes. In another embodiment of the invention, this technique can be used to monitor latent infection by other retroviruses through the use of primers that specifically recognize the LTR sequences of other retroviruses.

In another aspect of the present invention, there. i s provided a kit for detecting integrated retroviruses and/or determining the number of cells with integrated retroviruses in a human sample. The kit contains a primer for an Alu sequence, a primer for a retroviral sequence, a probe that specifically recognizes amplified retroviral sequence, and a detection agent that detects hybridization of the probe to amplified retroviral sequence. Preferably, the primer for the Alu sequence has the sequence 5'-GCCTCCCAAAGTGCTGGGATTACAG-3'(SEQ ID NO: 4), and the primer for the retroviral sequence recognizing the 5' LTR sequence of HIV has the sequence of 5'-AAGCTCGATATCAGCAGTTCT-3' (SEQ ID NO: 2). The kit can be used on samples of paraffin-embedded sections or frozen sections of blood, lymph nodes or lymphocytes. In another embodiment of the invention, the kit can be used to detect other integrated retroviruses and/or determining the number of cells with other integrated retroviruses by using primers that specifically recognize the LTR sequences of other retroviruses.

The following examples are given for the purpose of illustrating various embodiments of the invention and are not meant to limit the present invention in any fashion.

EXAMPLE 1

Cell Culture

Peripheral blood lymphocytes isolated from human blood by centrifugation through LSM were PHA-stimulated and grown in RPMI-1640 medium, supplemented with 15% FBS and 40 U/ml of IL-2. Uninfected cells served as negative controls and cultures infected with laboratory isolates of HIV (AC1 and R28) served as positive control samples. Also, CEM cells served as negative controls, while a clonal CEM line constitutively producing HIV (35.8 cells) (11) which harbor one to two copies of integrated HIV provirus served as positive control.

EXAMPLE 2

In situ PCR and Hybridization $3 \times 10^5$ cells in 50 μl of PBS were cytocentrifuged at 1000 rpm for 2 min onto glass slides. The slides were then dipped in 4% paraformaldehyde (PFA) at RT for 20 min. They were then transferred to 3×PBS (stop reaction) at RT for 2 min., to 1×PBS for 2 min., and transferred to fresh 1×PBS for 2 min. The slides were then dehydrated through 50%, 70%, and 100% ethanol for 4 min/each and allowed to air dry. The slides were heated at 100° C. at a heating block for 90 sec. and then treated with 0.3% $H_2O_2$ at RT overnight. The next day the slides were washed and immersed in diluted proteinase K in PBS (6 μg/ml) at RT for 5 min. The slides were heated at 95° C. for 2 min. to stop the reaction, rinsed in PBS for 10 min. and rinsed in $H_2O$ for 10 min. They were then air-dried. 50 μl of amplification cocktail (30.5 μl $dH_2O$, 5.0 μl 10×PCR buffer, 4.0 μl dNTP, 1.0 μl primer1, 1.0 μl primer2, 8.0 μl $MgCl_2$, 0.5 μl Taq) was added into each well, and a coverslip was carefully sealed around the edge. The slides were heated on a heating block at 92° C. for 90 sec. PCR was performed at 95° C. for 40 sec., 55° C. for 90 sec., and 72° C. for 90 sec. for 30 cycles. The slides were soaked in 100% ethanol and heated at 92° C. for 1 min. The slides were soaked in 2×SSC at RT for 5 min., and placed at 4° C. overnight. 100 μl of hybridization mix (50 μl deionized Formamide, 10 μl 20×SSC, 10 μl 100×Denhart's sol, 10 μl ssDNA (10 mg/ml), 10 μl 10% SDS, 4 μl $dH_2O$, and 6 μl probe (25–50 mg/ml)) was added into each well on the slide and heated at 95° C. for 5 min. Then slides were placed on ice for 1 min. and incubated at 42° C. for 2–4 hours with coverslips in a humid chamber. The slides were washed in 2×SSC at RT: 5 min×2 times, and 0.1×SSC at 42° C. for 10 min. The sections were dipped into buffer 1 (0.1M tris-HCl, 0.15M NaCl, pH 7.5) and covered with 20–40 μl buffer 2 (0.5% blocking reagent in buffer 1). Coverslips were added, and the slides were placed at RT for 15 min. The coverslips were removed and the slides were dipped in buffer 1. Twenty μl of diluted anti-Digoxigenin Ab 1:500 in buffer 2 was added to each slide, coverslipped, and incubated at RT in humid chamber for 1 hr. The coverslips were removed and the slides were washed with buffer 1: 10 min×2 times, and equilibrated for 5 min in buffer 3 (color detection B). 20 μl NBT/BCIP was added onto each section, and coverslips were replaced. The slides were incubated overnight in the dark and were observed the next day under a microscope.

EXAMPLE 3

Latent Infection in Cloned or Normal T Cells

Figure 2A:
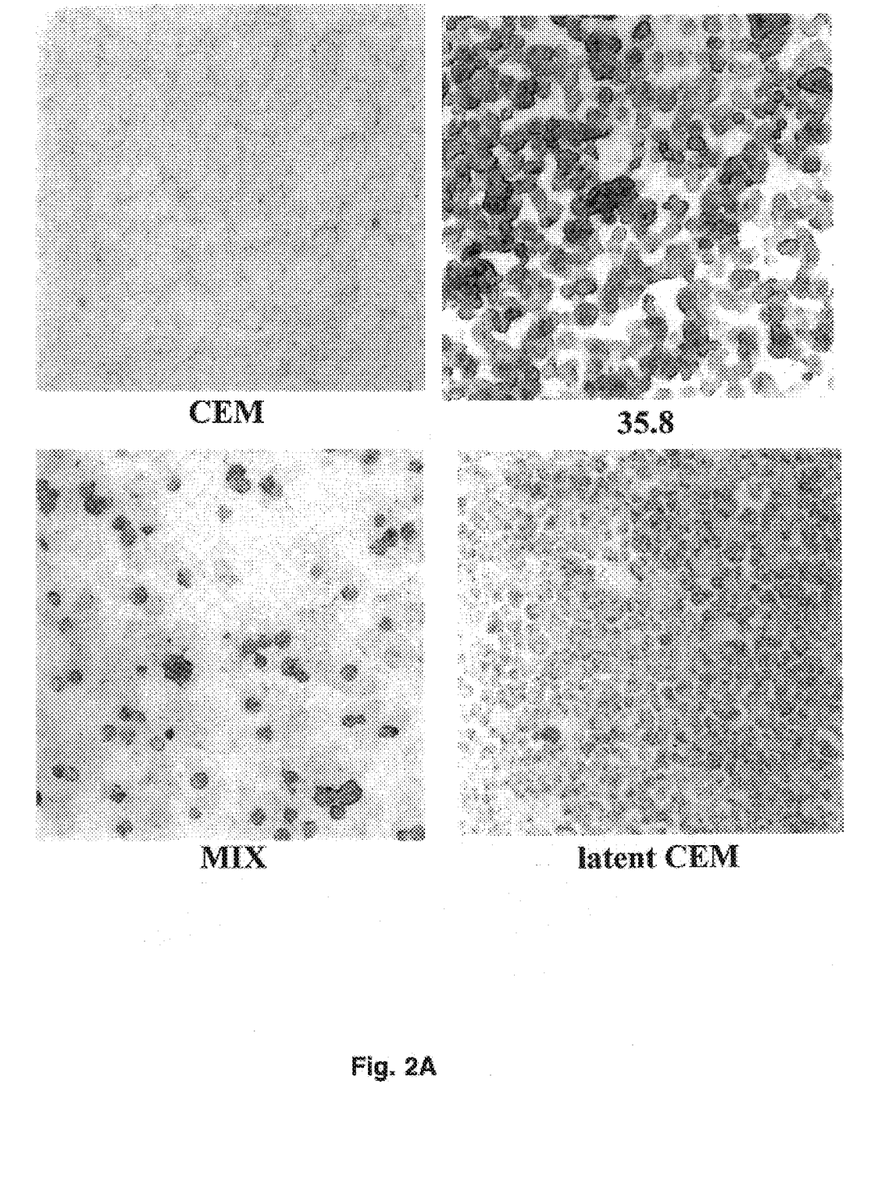
FIG. 2A shows results from in situ PCR-hybridization on uninfected CEM cells, productively-infected 35.8 cells, a fifty-fifty mixture of the two, and on HIV latently infected CEM cells. No reaction occurred in the uninfected cells, but strong reactions occurred in both the productively infected and latently infected cells.
Figure 2B:
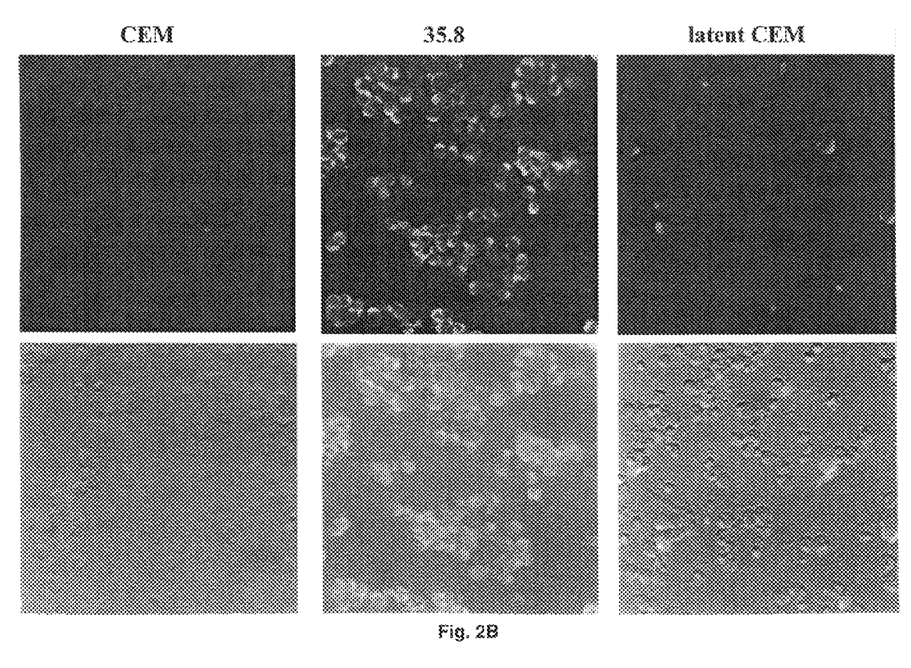
FIG. 2B shows HIV p24 immunostaining of CEM cell populations used in in situ PCR hybridization assays. Uninfected CEM cells (negative control); productively-infected 35.8 cells (positive control); latently-infected CEM cells show less than 5% of these cells are making HIV.
Figure 2C:
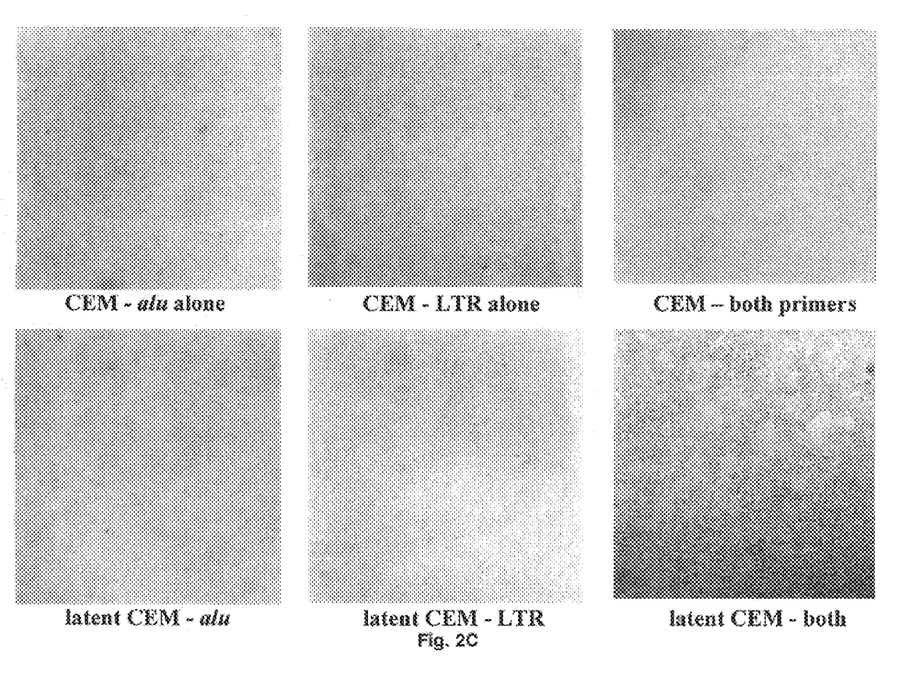
FIG. 2C shows in situ PCR-hybridization on CEM cells and latently-infected CEM with single primers alone. Performing the assay with only the alu primers or the LTR primers alone did not give any reaction.

Uninfected, latently-infected and productively-infected CEM T-cells were cytocentrifuged onto glass slides, fixed in paraformaldehyde, and the in situ PCR assay was performed as described. FIG. 2 shows that no reaction occurred in the uninfected cells (CEM), but strong blue reactions occurred in both of the chronically, productively-infected (35.8), as well as the latently infected cells. FIG. 2B shows which cells above were producing HIV by in situ fluorescent immunostaining for HIV p.24. Performing the PCR with only the Alu primer or the LTR primer alone did not give any reaction (FIG. 2C), and, therefore, this PCR assay appeared to be specific for the presence of HIV DNA. The majority of latently-infected cells were not making HIV P24 by in situ immunostaining (FIG. 2B).

Figure 3A:
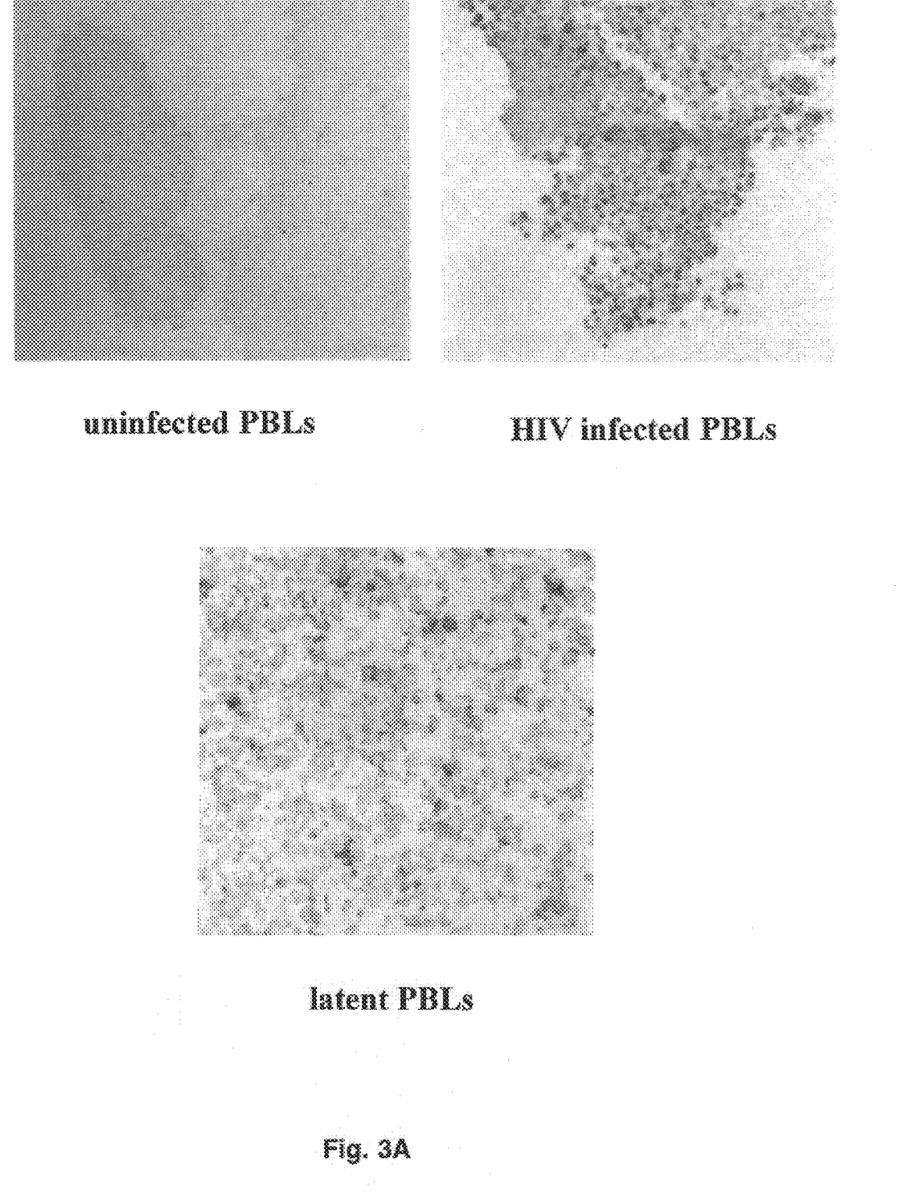
FIG. 3A shows in situ PCR-hybridization reactions on uninfected, acutely-infected, and latently-infected purified CD4 PHA-blasts. Cells were fixed and paraffin-embedded, and sections were made.
Figure 3B:
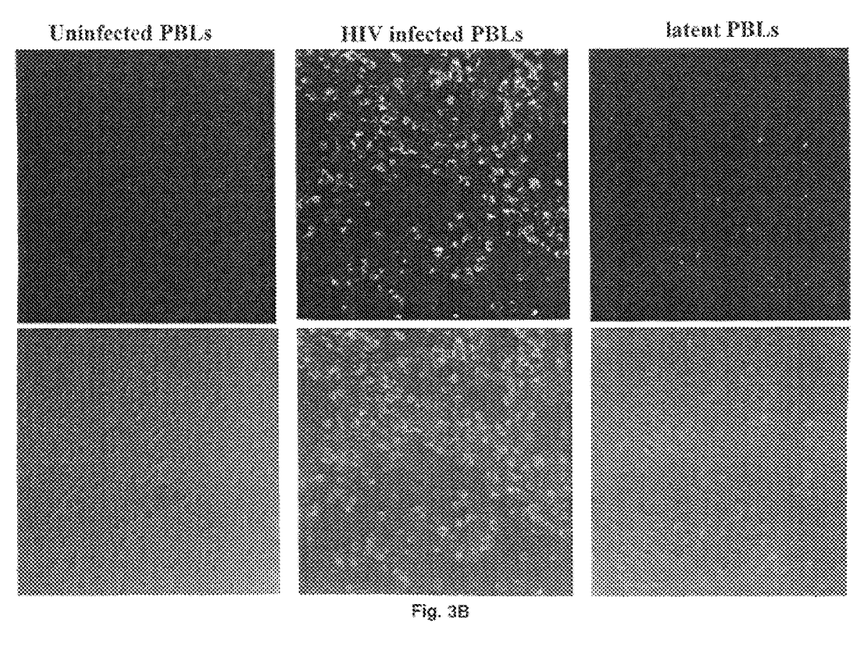
FIG. 3B shows HIV p24 immunostaining of uninfected, acutely-infected, and latently-infected purified CD4 PHA-blasts. The latently-infected PBLs are negative.

In situ PCR-hybridization reactions were also performed on uninfected and acutely-infected purified CD4 PHA-blasts. These cells were fixed, paraffin-embedded, and sectioned. Strong blue reactions occurred in infected lymphocytes but not in the uninfected cells (FIG. 3). Again, latently-infected PBLs were positive but P24-negative (FIG. 3B). Thus, the technique works well on paraffin-embedded normal lymphocytes.

Figure 4:
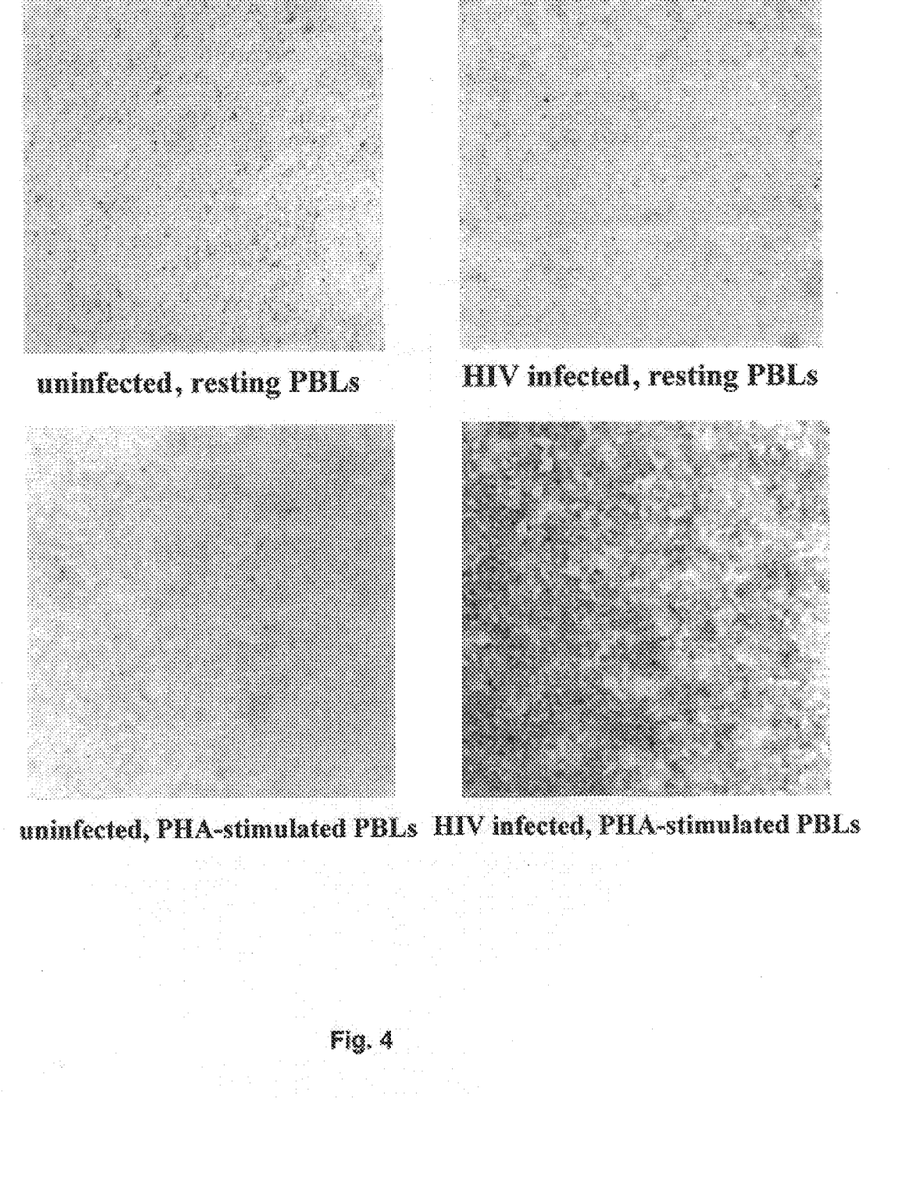
FIG. 4 shows acute abortive infection is negative by this assay. Resting CD4 lymphocytes were acutely infected and 18 hours later were cytocentrifuged onto glass slides and in situ PCR-hybridization was performed.
Figure 5:
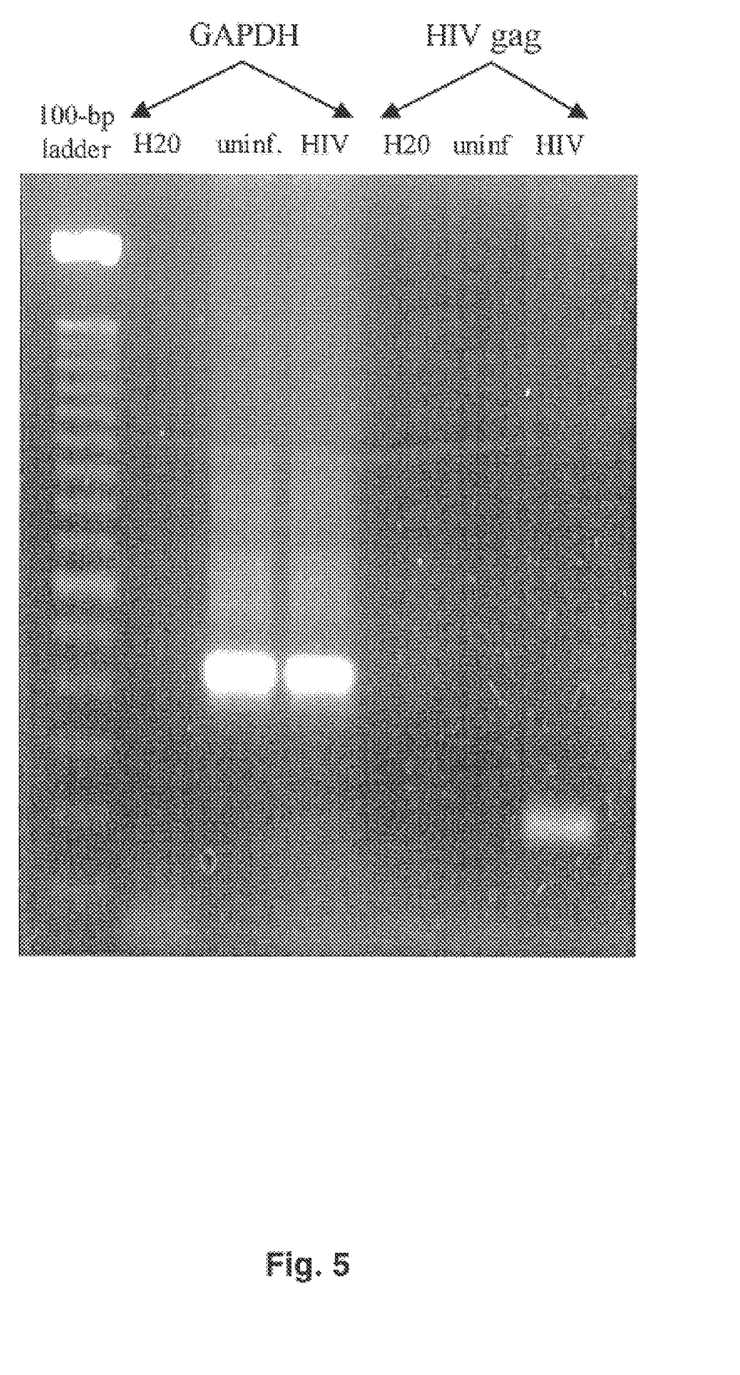
FIG. 5 shows standard DNA PCR on DNA extracted from the abortively infected resting cells in FIG. 4 using HIV gag primers. This shows that. HIV DNA is present in these cells but it is in the unintegrated form. DNA extracted from uninfected cells serve as a control.

To show definitively that this procedure only detects integrated HIV DNA, resting CD4 lymphocytes were acutely infected and 18 hrs later were cytocentrifuged onto glass slides, and the in situ PCR-hybridization was performed (FIG. 4). The abortively-infected resting cells were negative, but DNA extracted from the cells was HIV-DNA positive by routine PCR (FIG. 5). Thus, this in situ PCR-hybridization technique only detects integrated, not unintegrated, HIV DNA, The following references were cited herein:

1. Adams et al. (1994) Proc. Natl. Acad. Sci. USA. 91, 3862–6.
2. Butera et al. (1994) Journal of Virology 68, 2726–30.
3. Cannon et al. (1994) Journal of Virology 68, 1993–7.
4. Chen et al. (1994) Journal of Virology 68, 654–60.
5. Chun et al. (1997) Nature 387, 183–8.
6. Chun et al. (1997) Proc. Natl. Acad. Sci. USA. 94(24):13193–7.
7. Embretson et al. (1993) Nature 362, 369–372.
8. Finzi et al. (1999) Nature Medicine. 5(5):512–7.
9. Finzi et al. (1997) Science 278, 1295–300.
10. Folks et al. (1986) Science 231, 600–602.
11. Li et al. (1996) Virology 225, 196–212.
12. Piette and Legrand-Poels. (1994) Chemico-Biological Interactions 91, 79–89.
13. Pomerantz et al. (1990) Cell 61, 1271–1276.
14. Sonza et al. (1996) Journal of Virology 70(6), 3863–9.
15. Yang et al. (1993) AIDS Research & Human Retroviruses 9, 747–54.
16. Zack et al. (1990) Cell 61, 213–222.
17. Zack et al. (1992) Journal of Virology. 66(3):1717–25.

Any patents or publications mentioned in this specification are indicative of the levels of those skilled in the art to which the invention pertains. These patents and publications are herein incorporated by reference to the same extent as if each individual publication was specifically incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of in situ detection for integrated HIV in a human tissue sample, consisting the steps of:
   amplifying DNA in said sample with PCR using a primer of SEQ ID No. 2 or 3 that recognizes the LTR sequence of HIV and a primer for an Alu sequence, wherein said primer for Alu sequence has the sequence of SEQ ID No. 1;
   hybridizing the PCR-amplified DNA with a probe that specifically recognizes the amplified retroviral sequence; and
   detecting hybridization of the probe, wherein said hybridization indicates the presence of integrated HIV in said sample.

* * * * *

UNITED STATES PATENT AND TRADEMARK OFFICE
CERTIFICATE OF CORRECTION

PATENT NO. : 6,448,014 B2
DATED : September 10, 2002
INVENTOR(S) : Miles W. Cloyd, Chi-Cheng Yeh and Jianmin Chen It is certified that error appears in the above-identified patent and that said Letters Patent is hereby corrected as shown below:

Column 1,
Line 27, "i. e." should read -- i.e. --

Column 2,
Line 13, "o f" should read -- of --.
Line 15, "long-standing" should read -- longstanding --.
Line 48, "t o" should read -- to --.
Line 67, "alu" should read -- Alu --.

Column 3,
Line 17, "alu" should read -- Alu --.
Line 33, please delete the period after "that".
Line 35, "serve" should read -- serves --.
Line 41, "straight-forward" should read -- straightforward --.

Column 4,
Line 11, "$^{32}$p" should read -- $^{32}$P --.
Line 44, please delete the period after "there".
Line 44, "i s" should read -- is --.
Line 53, please insert a space before "(SEQ ID".

Column 5,
Lines 16 and 21, please insert a period after "min".
Line 49, "Twenty" should read -- 20 --.

UNITED STATES PATENT AND TRADEMARK OFFICE
CERTIFICATE OF CORRECTION

PATENT NO. : 6,448,014 B2
DATED : September 10, 2002
INVENTOR(S) : Miles W. Cloyd, Chi-Cheng Yeh and Jianmin Chen It is certified that error appears in the above-identified patent and that said Letters Patent is hereby corrected as shown below:

Column 6,
Line 2, "p.24" should read -- P24 --.
Line 19, please insert a period after "hrs".
Line 34, please align "Chun et al" with the left edge of the column.

Signed and Sealed this

Twelfth Day of August, 2003

JAMES E. ROGAN
*Director of the United States Patent and Trademark Office*

SEQUENCE LISTING

<160> NUMBER OF SEQ ID NOS: 4

<210> SEQ ID NO 1
<211> LENGTH: 23
<212> TYPE: DNA
<213> ORGANISM: artificial sequence
<220> FEATURE:
<221> NAME/KEY: primer
<223> OTHER INFORMATION: primer for the Alu sequence in the human
      chromosomal DNA

<400> SEQUENCE: 1
tcccagctac tggggaggtg agg                                                23

<210> SEQ ID NO 2
<211> LENGTH: 21
<212> TYPE: DNA
<213> ORGANISM: artificial sequence
<220> FEATURE:
<221> NAME/KEY: primer
<223> OTHER INFORMATION: primer for the retroviral sequence recognizing
      the 5' LTR sequence of HIV

<400> SEQUENCE: 2
aagctcgata tcagcagttc t                                                  21

<210> SEQ ID NO 3
<211> LENGTH: 22
<212> TYPE: DNA
<213> ORGANISM: artificial sequence
<220> FEATURE:
<221> NAME/KEY: primer
<223> OTHER INFORMATION: primer for the retroviral sequence recognizing
      the 3' LTR sequence of HIV

<400> SEQUENCE: 3
cagctgcttt ttgcctgtac tg                                                 22

<210> SEQ ID NO 4
<211> LENGTH: 25
<212> TYPE: DNA
<213> ORGANISM: artificial sequence
<220> FEATURE:
<221> NAME/KEY: primer
<223> OTHER INFORMATION: primer for the Alu sequence in the human
      chromosomal DNA

<400> SEQUENCE: 4
gcctcccaaa gtgctgggat tacag                                              25